United States Patent [19]

Klipa et al.

[11] Patent Number: 4,886,922

[45] Date of Patent: Dec. 12, 1989

[54] CATALYST FOR DEHYDROHALOGENATION

[75] Inventors: Dennis K. Klipa, Midland; James R. Dewald, Bay City, both of Mich.

[73] Assignee: The Dow Chemical Company, Midland, Mich.

[21] Appl. No.: 650,915

[22] Filed: Sep. 14, 1984

[51] Int. Cl.$^4$ ............................................. C07C 17/34
[52] U.S. Cl. ..................................... 570/193; 570/200; 570/204
[58] Field of Search ................ 570/193, 200, 204, 143

[56] References Cited

U.S. PATENT DOCUMENTS

| | | | |
|---|---|---|---|
| 2,518,409 | 8/1950 | Williamson | 502/31 |
| 2,746,842 | 5/1956 | Block et al. | 502/355 |
| 2,778,861 | 1/1957 | Kundiger et al. | 570/193 |
| 3,141,896 | 7/1964 | Stein | 502/355 |
| 3,299,152 | 1/1967 | Inaba et al. | 570/227 |
| 3,773,691 | 11/1973 | Leach | 502/355 |
| 4,205,015 | 5/1980 | Wang et al. | 570/193 |
| 4,287,089 | 9/1981 | Convers et al. | 34/9 |

FOREIGN PATENT DOCUMENTS

| | | | |
|---|---|---|---|
| 11003 | of 1971 | Japan | 570/227 |
| 642282 | 1/1979 | U.S.S.R. | 570/227 |

*Primary Examiner*—Werren B. Lone

[57] ABSTRACT

A method for preparing an α-substituted styrene such as 2-(3,5-dichlorophenyl)-4,4,4-trichloro-1-butene comprising contacting, an α-haloalkylbenzene such as 3-(3,5-dichlorophenyl)-1,1,1,3-tetrachlorobutane with a catalyst consisting essentially of γ-alumina dried to a moisture content between about zero to about 12% by weight, the γ-alumina serving to catalyze the dehydrohalogenation of the α-haloalkylbenzene to produce the α-substituted styrene.

28 Claims, No Drawings

CATALYST FOR DEHYDROHALOGENATION

BACKGROUND OF THE INVENTION

This invention relates to methods for preparing α-substituted styrenes. α-(1-haloalkyl)styrenes are taught in U.S. Pat. No. 3,391,203 to be useful as parasiticides and insecticides. They are also known to be useful intermediates in the manufacture of other biologically-active compounds such as herbicides, as taught in U.S. Pat. No. 3,373,011. In preparing α-substituted styrenes, U.S. Pat. No. 4,188,346 discloses that the Lewis acid SbCl$_5$ alone was a good catalyst, but it was later shown to be difficult to remove and detrimental to subsequent epoxidations. U.S. Pat. No. 4,205,015 discloses a method for preparing α-substituted styrenes using a catalyst such as AlCl$_3$ deposited on an inert support such as silica gel or alumina. However, this catalyst suffers the shortcomings of requiring additional time and expense to prepare the catalyst, and has noxious fumes safety problems associated with undesirably high levels of noxious fumes such as hydrogen halide.

In view of the deficiencies of prior art methods, it would be highly desirable to provide an improved method for making α-substituted styrenes.

SUMMARY OF INVENTION

In accordance with the present invention, α-substituted styrenes are advantageously obtained by contacting an α-haloalkylbenzene with a catalyst consisting essentially of γ(gamma)-alumina, the γ-alumina serving to catalyze dehydrohalogenation of the α-haloalkylbenzene to produce an α-substituted styrene. The present invention has the advantage of utilizing a catalyst which requires less time and expense to prepare compared with other methods previously taught. Another advantage of the present invention is the improvement in safety over other methods by eliminating the levels of noxious fumes such as hydrogen halide produced during catalyst preparation. Another advantage of the present invention is that it simplifies the preparation of the catalyst over other methods previously taught. The α-substituted styrenes produced in the practice of this invention are useful as biologically active compounds as described hereinbefore and as intermediates in the preparation of other biologically-active compounds. And still yet another advantage of the present invention is that it provides a method for making α-substituted styrenes in a yield and purity as good or better than that taught by other methods while also enjoying the above listed other advantages.

DETAILED DESCRIPTION OF THE EMBODIMENTS

For the purposes of this invention, an α-haloalkylbenzene is an aromatic compound consisting of a polyhaloalkyl substituent bonded to a phenyl group having one or more ring substituents. In said polyhaloalkyl substituent, one halogen (hereinafter called a benzylic halogen) is bonded to the α-alkyl carbon bonded to the phenyl group, and at least one other halogen (hereinafter called a non-benzylic halogen) is bonded to one other alkyl carbon. The substituent or substituents of the phenyl ring can include hydrogen, halo, nitro, alkyl, alkoxy, alkylthio, aryl, aryloxy, sulfur containing groups, carboxy, alkoxy, carbonyl, haloalkyl including polyhaloalkyl such as CF$_3$, haloaryl, and other substituent groups, all of which will not interfere with dehydrohalogenation reactions which are catalyzed by the γ-alumina. In any event, such substituents should be substantially inert during such dehydrohalogenation reactions. The terms halo or halogen are meant to refer generally to fluorine, chlorine, bromine and iodine. The preferred halogens are chlorine and bromine. Chlorine is generally most preferred on account of the relative cost of the other halogens.

Preferred α-haloalkybenzenes, for the purposes of this invention, are represented by formula (I)

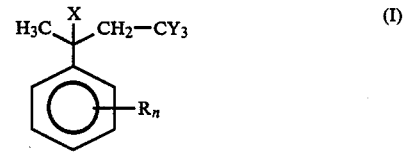

wherein each R is individually halo, hydrogen, alkyl, haloalkyl, including polyhaloalkyl such as —CX$_3$ (eg., —CF$_3$) or substituted alkyl and n is 0 to the maximum number of remaining available ring positions on the aromatic ring. More preferably, R is individually halo such as chloro, bromo, fluoro, or iodo, and n is from 1 to 3. Most preferably, n is 2 and each R is individually chloro substituted at the 3 and 5 positions on the ring. X is halo such as chloro, bromo, fluoro, or iodo. More preferably, X is chloro or bromo, most preferably chloro. Each Y is independently the same or different halogen, so that Y$_3$ maybe such as —Cl$_3$ —Br$_3$ —F$_3$, —I$_3$, —Cl$_2$Br, —Br$_2$Cl, Cl$_2$I. More preferably, Y$_3$ is —Cl$_3$ and —Br$_3$, and most preferably is —Cl$_3$.

Examples of especially preferred α-haloalkylbenzenes include 3-(3,5-dichlorophenyl)-1,1,1,3-tetrachlorobutane(DCTCB) and 3-bromo-(3,5-dichlorophenyl)-1,1,1-trichlorobutane.

α-haloalkylbenzenes are suitably prepared by any known method. For example, α-methylstyrene or arylsubstituted methylstyrene, prepared in accordance with one of the procedures described in U.S. Pat. No. 2,816,934 to Stempel, is reacted with a polyhaloalkane such as carbon tetrachloride, bromotrichloromethane, methylene chloride or dichloronitromethane in the presence of an amine and cuprous chloride by the procedure described in U.S. Pat. No. 3,454,657 to produce a desired α-haloalkylbenzene.

Suitable γ-alumina catalysts include χ(chi)alumina, boehmite or any combination thereof. The α(alpha), κ(kappa), ξ(delta), or θ(theta) aluminas will not promote dehydrohalogenation as well as γ-alumina and thus are not as practical for commercial applications.

The γ-alumina must be dried to the proper moisture content to provide the proper catalytic action for dehydrohalogenation. Moisture content of the γ-alumina is determined by comparing the difference in weight between γ-alumina not heated and γ-alumina heated in a vacuum oven at a temperature of about 150° C. at a pressure of about 30 torr for about 24 hours. γ-Alumina may have a moisture content from about zero to about 12% by weight. More preferably the γ-alumina has a moisture content of about 2 to about 6% by weight, most preferably a moisture content of about 3% by weight. Advantageously, the γ-alumina is in the form of a particulate solid, preferably one having an average particle diameter in the range of about 80 to 200 mesh (U.S. Sieve Series).

The γ-alumina may be made by heating gibbsite at temperatures of from about 100° C. to about 150° C. Gibbsite is a naturally occuring polymorphic form of aluminum hydroxide, Al(OH)₃, or aluminum trihydrate, Al₂O₃·3H₂O, as defined in X-Ray Identification and Crystal Structures of Clay Minerals. G. W. Brindley, (ed.), chapter 10, pages 244-256. Alternatively γ-alumina may be obtained commercially as F-1 ® alumina (trademark of the Aluminum Company of America). X-ray diffraction analysis of the F-1 alumina showed it to be a γ-type alumina having primarily two phases: χ-alumina and Boehmite alumina.

Drying the γ-alumina to the proper moisture content is critical to the present invention since the presence of water in or on the γ-alumina will inhibit the dehydrohalogenation process. The γ-alumina may be dried by distilling off the water with an organic solvent to form an azeotrope mixture of the water/organic solvent. Halocarbon or hydrocarbon solvents may be used to form the azeotrope mixture. In practicing the invention, the amount of water remaining in the azeotrope mixture was determined by visually observing the separated phases of the solvent and water condensed on the glass condenser.

Hydrocarbon solvents for drying the γ-alumina preferably include benzene, toluene, ethylbenzene, heptane, decane, cyclohexane, or mixtures thereof. Halocarbon solvents preferably include chloroform, carbon tetrachloride, chlorobenzene, dichlorobenzene, trichlorobenzene, 1,1,1-trichloroethane, 1,2-dichloroethane, or mixtures thereof. Most preferably, the halocarbon solvent is chlorobenzene or carbon tetrachloride.

Alternatively, the γ-alumina may be dried by heating it in a vacuum oven at a temperature of about 150° C. at a pressure of about 30 torr for about 24 hours.

The method for preparing any of the α-substituted styrenes from the requisite haloalkyl benzene compounds may be conducted neat, i.e. in the absence of a solvent. Preferably, the method is performed using a solvent, such as any of the hydrocarbon or halocarbon solvents listed above for drying the γ-alumina.

In the practice of the the present invention, a desired α-substituted styrene is prepared by contacting the requisite α-haloalkylbenzene with γ-alumina at an elevated temperature, the γ-alumina serving to catalyze the dehydrohalogenation of the α-haloalkylbenzene to produce the corresponding α-substituted styrene. The γ-alumina may constitute between about 0.1 to about 99% by weight of the combined weight of the γ-alumina and α-haloalkylbenzene present in the reaction mixture. More preferably the the γ-alumina is between about 1 to about 15% of the weight of γ-alumina and the α-haloalkylbenzene in the reaction mixture. Most preferably the weight of the γ-alumina is between about 5 to about 10% by weight of the γ-alumina and α-haloalkylbenzene.

Preferably, the catalyzed reaction is completed in a time of about 0.5 to about 16 hours to give the desired α-substituted styrene. More preferably, the reaction is completed in about 5 to about 12 hours.

In carrying out the catalyzed reaction the γ-alumina may be utilized in the form of a fixed bed through which the α-haloalkylbenzene is passed or circulated. The fixed bed is prepared by mounting a fitted support permeable to fluids within a tube. The γ-alumina is placed atop the fritted support and an other fritted support is place atop the alumina. The solvent containing the α-haloalkylbenzene is, or the α-haloalkylbenzene alone if being reacted neat, then passed upwardly through the tube to contact the γ-alumina, forming the desired α-substituted styrene. Alternatively and more preferably, the γ-alumina is used in the form of a slurry or a mixture thereof with solvent medium containing the α-haloalkylbenzene.

The method for preparing the α-substituted styrene may be advantageously conducted at a temperature in the range of about 40° C. to about 160 ° C. More preferably the method is conducted at temperatures between about 75° C. to about 90° C., most preferably at about 82° C.

The method advantageously may be performed at ambient pressures of about 760 torr. Preferably the method is performed at lower pressures of about 300 to about 760 torr. At lower pressures the hydrogen halide gas, a by-product of the reaction, is removed from the γ-alumina, thus enhancing the rate of formation of the α-substituted styrene.

After the α-haloalkylbenzene is contacted with the γ-alumina, the reaction begins immediately, as evidenced by evolution of hydrogen halide gas. Hydrogen halide gas can be detected by contacting the evolving gas with NH₃ vapors eg; in the case of HCl gas forming a white smoke of NH₄Cl, which is easily observed. Alternatively, wet litmus paper can be used to detect evolution of hydrogen halide. Where the γ-alumina is used as a slurry, the reaction mixture is agitated sufficiently to keep the γ-alumina in suspension until the dehydrohalogenation reaction is completed.

After formation of an α-substituted styrene by the present invention, the product is separated from the α-alumina catalyst by filtration and then, if necessary, by fractionally distilling off any solvents that may be present.

The product of the dehydrohalogenation reaction is primarily an α-substituted styrene wherein the benzylic halogen and the said hydrogen on an adjacent carbon have been eliminated as HCl. In embodiments of particular interest, the α-substituted styrene is represented by formula (II):

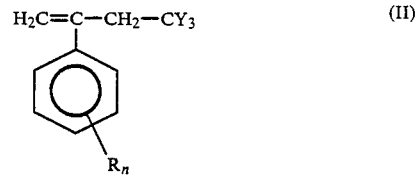

wherein R, Y and n are defined as hereinbefore. An especially preferred α-substituted styrene is 2-(3,5-dichlorophenyl)-4,4,4-trichloro-1-butene(DCTCS).

The following examples are given to illustrate the invention and should not be construed as limiting its scope. All percentages in the examples are by weight unless otherwise indicated.

EXAMPLE 1

Preparation of DCTCB

A 3-necked, round bottomed flask (1 liter) fitted with reflux condenser, internal thermometer, addition funnel, mechanical stirrer and heating mantle was charged with 515 milliliters (ml) CCl₄ and 0.53 grams (g) CuCl and then heated to reflux (78° C.). A solution of 200 g of 3,5-dichloro-α-methylstyrene and 5.61 ml t-butylamine was added. The mixture was refluxed for 8.5 hours.

After HCl sparge and suction filtration, the filtrate volume was 660 ml. The filtrate was evaporated at 50°-60° C. with an aspirator vacuum until the solvent was removed. Analysis of this residue by gas liquid chromatagraphy (GLC) showed that it contained 94.5% DCTCB.

Preparation of DCTCS

To a 3-necked, round bottomed flask fitted with a thermometer, temperature controller, heating mantle, reflux condenser, addition funnel and mechanical stirrer was added CCl$_4$ and F-1 alumina, which was previously dried at a temperature of 150° C. under reduced pressure. The mixture was heated to reflux and DCTCB as prepared above was added. After a short period of time vapors of HCl were observed exiting the reflux condenser. When the reaction was complete, as judged by GLC analysis, the alumina was removed by filtration and the CCl$_4$ was evaporated under reduced pressure to give the product DCTCS, i.e., 2-(3,5-dichlorophenyl)-4,4,4-trichloro-1-butene represented by the formula:

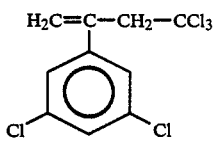

EXAMPLE 2

To a 3-necked, round bottomed flask fitted with thermometer, temperature controller heating mantle, reflux condenser, addition funnel and mechanical stirrer was added CCl$_4$ and F-1 alumina. The F-1 alumina catalyst was dried by distilling off the H$_2$O/CCl$_4$ azeotrope mixture until only CCl$_4$ vapors were coming overhead. To this in-situ prepared catalyst in CCl$_4$, which is maintained at the appropriate reaction temperature, was added DCTCB prepared in accordance with Example 1. After a short period of time, vapors of HCl were observed exiting the reflux condenser. When the reaction was complete as judged by GLC analysis, the alumina was removed by filtration and the CCl$_4$ was evaporated under reduced pressure to give crude DCTCS.

EXAMPLE 3

To a two-liter, 3-necked, round bottomed flask fitted with a reflux condenser, mechanical stirrer, thermometer, temperature controller, heating mantle, and addition funnel was added F-1 alumina (53.3 g) and CCl$_4$ (467 ml). This was brought to reflux and H$_2$O was seen condensing on the coils of the condenser. Then the addition of a solution of DCTCB (400 g) in CCl$_4$ (267 g) was started. No HCl vapor was observed after 40 ml of DCTCB was added. Then the H$_2$O present was removed by azeotropic distillation with CCl$_4$. About 65 ml of CCl$_4$ was distilled off and then 65 ml of fresh dry CCl$_4$ was recharged to the round bottomed flask. When the 65 ml of CCl$_4$ had been removed the reaction started. After 80 minutes a sample of the reaction mixture was taken which showed very little DCTCB. The heating mantle was removed after a total reaction time of 100 minutes. After cooling, the reaction mixture was filtered to remove the alumina. The solvent was evaporated under reduced pressure. The resulting DCTCS product had an assay of 85%.

EXAMPLE 4

To a one liter, 3 necked round bottomed flask fitted with an addition funnel, reflux condenser, and thermometer, temperature controller, heating mantle was added F-1 alumina (36 g) and CCl$_4$ (315 ml). The catalyst slurry was stirred and heated to reflux. The 60 ml of CCl$_4$ was distilled off to remove H$_2$O and then 60 ml of fresh, dry CCl$_4$ was added. The addition of a 71% solution of crude DCTCB in CCl$_4$ (270 g) was started but no HCl came off immediately. Additional water was observed collecting on the coils of the reflux condenser so 5 ml more CCl$_4$ was distilled off and the condenser was removed, rinsed with dry acetone, and replaced. HCl evolution then started and the DCTCB was then completely added in about 5 minutes. After 90 minutes of reaction time, the heating mantle was removed and analysis of the reaction mixture showed no DCTCB remaining. The reaction mixture was cooled to below 30° C. and filtered to remove the alumina. The filter cake was washed once with 100 ml CCl$_4$ and the filtrates were combined. The solvent was removed under reduced pressure to give a product with DCTCS assay of 88%.

EXAMPLE 5

The same procedure as in Example 4 was used except that recrystallized DCTCB was used. After replacing the 60 ml of CCl$_4$ distilled off at the outset, the DCTCB addition was started but no HCl was observed again. Then 5 ml more of CCl$_4$ was distilled off and the condenser was rinsed with acetone and dried before being replaced. Then HCl evolution began. The addition of the DCTCB solution (270 g DCTCB in 180 g CCl$_4$) was completed in about 5 min. After 1 hr. the HCl evolution was slow and a sample taken for analysis showed no DCTCB remaining. The heat was removed after 1 hr. and 20 minutes reaction time. The reaction mixture was cooled to below 30° C. and filtered to remove the alumina catalyst. The cake was washed once with 100 ml CCl$_4$ and the filtrates were combined. The solvent was removed under reduced pressure to give crude DCTCS with a 93.7% assay.

EXAMPLE 6

To a 250 ml 3-necked flask fitted with a thermometer, temperature controller, heating mantle, mechanical stirrer, reflux condenser and addition funnel was added 70 ml of CCl$_4$ and dried F-1 alumina (8.0 g). The mixture was brought to reflux and after about 30% of a solution of 60 g DCTCB in 84.5 g CCl$_4$ had been added, the addition was stopped to allow reflux. Within 3 minutes of the start of the addition of DCTCB solution, HCl was observed exiting the top of the condenser. Addition of reactant was completed in about 5 minutes. After 45 minutes of reaction, analysis of a sample of the reaction mixture showed no DCTCB remaining. After another fifteen minutes heating was stopped and the product was cooled and then filtered to remove the alumina. The solvent was removed under reduced pressure to give a product, which had a DCTCS assay of 88.7%.

EXAMPLE 7

In still another preparation according to the invention for the procedure used was the same as in Example 6, except deviations from that example described here. Only 3.6 g of dried F-1 alumina was used. Within 3 minutes of initial addition of DCTCB to the F-1 alumina the HCl was coming out of the condenser. After 45 minutes the HCl evolution was evident (visually by fuming white smoke with NH3 vapors) and was faster than Example 6 which was run simultaneously. The heat was removed from the reaction mixture and the stirring stopped after 1 hour. Analysis of the reaction sample showed 1% DCTCB remaining. The reaction mixture was filtered to remove the alumina. The solvent was removed under reduced pressure to give a product with DCTCS assay of 88.4%.

EXAMPLE 8

The catalyst used was F-1 alumina dried in a vacuum oven at 150° C.-20 torr for 24 hrs. To a 250 ml round bottomed 3-necked flask fitted with a mechanical stirrer, thermometer-temperature controller-heating mantle, addition funnel and reflux condenser was added CCl4 (70 ml) and F-1 alumina (3.6 g). This was brought to 70° C.±3° C. and a 71% solution of DCTCB is CCl4 (84.5g) was added over a 5 minute period. After 10 minutes the first traces of HCl were observed. Analysis of samples taken showed 57% conversion after 2 hours and 84% conversion after 4 hour to DCTCB.

EXAMPLE 9

The same procedure was used as in Example 8 except only 1.8 g of F-1 alumina was added. Addition of 71% solution of DCTCB in CCl4 (84.5 g) was carried out over a 5 minute period. After 15 minutes the first very faint whisps of HCl could be detected. Analysis of samples showed 8% conversion after 2 hours and 16% conversion after 4 hrs. The solution of DCTCB was from the same source as that used in Example 8.

EXAMPLE 10

To a 250 ml 3-necked, round bottomed flask fitted with a reflux condenser, temperature controller, thermometer, heating mantle and mechanical stirrer was added CCl4 (70 ml) and a 71% solution of DCTCB in CCl4 (84.5 g). This was heated to 70° C. and the F-1 alumina, catalyst (3.6 g) was added all at once. Analysis of samples taken at 35, 95 and 120 min showed conversions of 53, 79 and 85%, respectively.

EXAMPLE 11

The procedure for this run was the same as Example 10 except that the reaction was held at 70° C. and the solvent refluxed by reducing the pressure. The catalyst was again solvent added all at once. Analysis of samples taken at 35, 95 and 120 min. showed conversions of 67, 94 and 98%, respectively.

Upon repeating Examples 1-11 using γ-alumina prepared from gibbsite according to the techniques described hereinbefore, substantially the same excellent results are obtained with respect to yield and purity of α-substituted styrene produced.

Further modifications of the invention herein disclosed will occur to persons skilled in the art and all such modifications are deemed to be within the spirit and scope of the invention as defined by the appended claims.

What is claimed is:

1. The method for preparing an α-substituted styrene of the formula

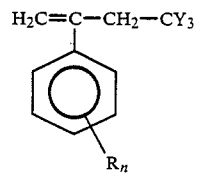

wherein R represents halogen, hydrogen, alkyl, haloalkyl, polyhaloalkyl or substituted alkyl; n is 0 to the maximum number of remaining available position on the aromatic ring; and each Y independently represents halogen;

comprising contacting a catalyst consisting essentially of dried γ-alumina with an α-haloalkylbenzene of the formula

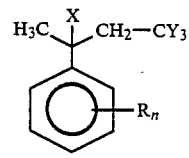

wherein X is halo, and $R_n$ and Y are defined as hereinbefore, said γ-alumina serving to catalyze the dehydrohalogenation of said α-haloalkylbenzene to said α-substituted styrene.

2. The method of claim 1, wherein said γ-alumina is χ-alumina, boehmite, or a combination thereof.

3. The method of claim 1, wherein said γ-alumina is dried to a moisture content of about zero to about 12% by weight.

4. The method of claim 1, wherein said γ-alumina is dried to a moisture content of about 2 to about 6% by weight.

5. The method of claim 1, wherein said γ-alumina is dried to a moisture content of about 3% by weight.

6. The method of claim 1, wherein said α-haloalkylbenzene is 3-(3,5-dichlorophenyl)-1,1,1,3-tetrachlorobutane and said α-substituted styrene is 2-(3,5-dichlorophenyl)-4,4,4-trichloro-1-butene.

7. the method of claim 1 wherein said α-haloalkylbenzene is 3-bromo-3-(3,5-dichlorophenyl)-1,1,1 trichlorobutane and said α-substituted styrene is 2-(3,5-dichlorophenyl)-4,4,4-trichloro-1-butene.

8. The method of claim 1, wherein said method is conducted in the absence of a solvent.

9. The method of claim 1, wherein said α-haloalkylbenzene is contacted with said γ-alumina in the presence of a solvent.

10. The method of claim 9, wherein said solvent is a hydrocarbon solvent selected from the group consisting of benzene, toluene, ethyl benzene, heptane, decane, cyclohexane, and mixtures thereof.

11. The method of claim 9, wherein said solvent is a halocarbon solvent selected from the group consisting of chloroform, carbon tetrachloride, chlorobenzene, dichlorobenzene, trichlorobenzene, 1,1,1-trichloroethane, 1,2-dichloroethane, and mixtures thereof.

12. The method of claim 11 wherein said halocarbon solvent is chlorobenzene.

13. The method of claim 11 wherein said halocarbon solvent is carbon tetrachloride.

14. The method of claim 1 wherein said γ-alumina is obtained by heating gibbsite at a temperature of about 150° C. at a pressure of about 30 torr for about 24 hours.

15. The method of claim 1, wherein said γ-alumina is dried by distilling off the water from the γ-alumina with an organic solvent.

16. The method of claim 15 wherein the organic solvent is a hydrocarbon or halocarbon solvent.

17. The method of claim 1 performed at temperatures between about 40° C. to about 160° C.

18. The method of claim 1, performed at temperatures between about 75° C. to about 85° C.

19. The method of claim 1 performed at about 82° C.

20. The method of claim 1 performed at a pressure of about 70 torr.

21. The method of claim 1 performed at a pressure of about 300 to about 760 torr.

22. The method of claim 1 wherein the amount of said γ-alumina used is between about 0.1 to about 99% by weight of the combined weight of γ-alumina and α-haloalkylbenzene.

23. The method of claim 1, wherein the amount of said γ-alumina used is between about 6 to about 20% by weight of the combined weight of γ-alumina and α-haloalkylbenzene.

24. The method of claim 1, wherein the amount of said γ-alumina is about 10 percent by weight of the combined weight of γ-alumina and α-haloalkylbenzene.

25. The method of claim 1 wherein said γ-alumina is retained in a fixed bed during the reaction.

26. The method of claim 1 wherein said γ-alumina is in utilized in a slurry with the α-haloalklybenzene.

27. The method of claim 9, further comprising separating said α-substituted styrene from said γ-alumina and said solvent.

28. The method of claim 27, wherein said γ-styrene is separated from said γ-alumina and said solvent by filtering the γ-alumina and fractionally distilling off the solvent.

* * * * *